United States Patent [19]

Kurz

[11] Patent Number: 4,505,672
[45] Date of Patent: Mar. 19, 1985

[54] TWO-PIECE GNATHOLOGIC ORTHODONTIC POSITIONER

[76] Inventor: Craven H. Kurz, 465 N. Roxbury Dr. #1011, Beverly Hills, Calif. 90210

[21] Appl. No.: 551,410

[22] Filed: Nov. 14, 1983

[51] Int. Cl.³ .............................................. A61C 7/00
[52] U.S. Cl. ...................................................... 433/6
[58] Field of Search .................................... 433/6, 215

[56] References Cited

U.S. PATENT DOCUMENTS

| | | | |
|---|---|---|---|
| 3,536,069 | 10/1970 | Gores | 433/6 |
| 3,675,327 | 7/1972 | Huget | 433/215 |
| 3,837,081 | 9/1974 | Kesling | 433/6 |
| 4,330,273 | 5/1982 | Kesling | 433/5 |
| 4,413,978 | 11/1983 | Kurz | 433/6 |

Primary Examiner—Robert Peshock
Attorney, Agent, or Firm—Keith D. Beecher

[57] ABSTRACT

A gnathologic orthodontic positioner which is split to provide an upper section for the maxillary arch and a separate lower section for the mandibular arch, the two sections being held together by elongated resilient members, such as elastics and/or by magnetic force. The upper and lower sections are attached to the teeth by mechanical clasps which may be assisted by suction cups.

5 Claims, 2 Drawing Figures

TWO-PIECE GNATHOLOGIC ORTHODONTIC POSITIONER

BACKGROUND OF THE INVENTION

Orthodontic tooth positioning appliances, such as the gnathologic positioner of the present invention are used in the final orthodontic treatment stages following the removal of the fixed orthodontic appliances. The positioner usually takes the form of a rubber of rubber-like mouthpiece with sockets formed in its top and bottom to receive the teeth of the patient. When the patient bites against the mouthpiece, the teeth are biased into their desired final positions by the orientations of the sockets.

Specifically, the prior art orthodontic positioner consists of an arch-shaped body made of any suitable natural or synthetic rubber, or appropriate plastic. Upper and lower archways are formed in the body, with each of the archways containing a plurality of tooth sockets corresponding in number to the teeth of the patient, the tooth sockets being arranged in an ideal relationship relative to the teeth of both the upper and lower arches of the patient. When the patient bites into the positioner, the necessary forces are applied to the teeth to bring the teeth to their desired ultimate positions.

A problem which is encountered in the prior art orthodontic positioners of the type described in the preceding paragraphs is that they are ineffective when the patient relaxes his or her jaw, which occurs, for example, when the patient is asleep or is concerned with other matters. The principal objective of the present invention is to provide a novel type of orthodontic gnathological positioner in which this problem is overcome.

The foregoing is achieved by making the positioner of the invention in two pieces with an upper section and a lower section, the two sections being held in traction to one another by resilient and/or magnetic forces. The upper and lower sections of the positioner of the invention are attached to the teeth by resilient mechanical clips, or clasps, which may be aided by small suction cups. The positioner of the present invention causes the jaws of the patient always to be biased to a closed position biting into the positioner, and overcoming any tendency for the patient to relax his or her jaw, so that the combination of the invention provides a better and faster arch coordination and occlusion seating. The traction that is provided by the resilient and/or magnetic forces creates an extrusive force on the opposing dentitions that results in an excellent occlusion seating feature.

DETAILED DESCRIPTION OF THE ILLUSTRATED EMBODIMENT

Figure 2:
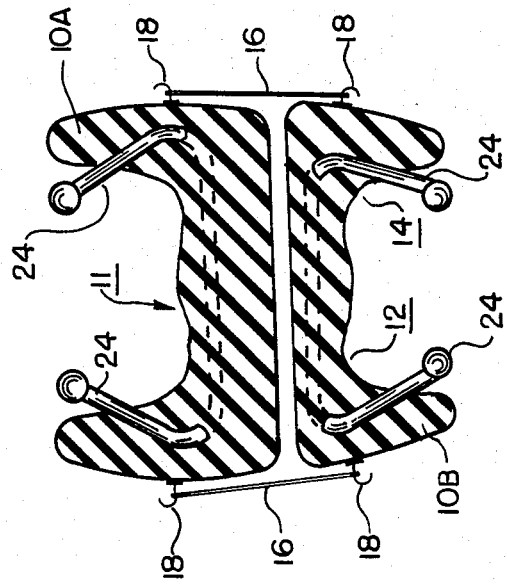
FIG. 2 is a section through the positioner of FIG. 1 taken essentially along the lines 2—2 of FIG. 1.

Referring now to the drawings, the tooth positioning and retaining appliance of the invention includes a pair of resilient arch-shaped members 10a, 10b which together form an orthodontic appliance. The member 10a has an upper archway 11, and the lower section 10b has a lower archway 12. The upper archway includes a number of tooth sockets 13 corresponding in number to the number of teeth of the patient's maxillary arch. The lower archway 12 of section 10b has a number of tooth sockets 14, corresponding in number to the teeth of the patient's mandibular arch. The tooth sockets are arranged in an ideal arch relationship to both the upper and lower arches of the patient, so as to apply the necessary forces to the teeth of the patient to bring the teeth into the desired ultimate positions.

The two sections are held together, for example, by resilient members such as elastics 16 which are supported on hooks 18 attached to the upper and lower sections.

The elastics 16 force the two sections 10a and 10b together, with the sections being maintained in proper alignment by interacting guides 20 and guideways 22 in the respective lower and upper sections.

The upper and lower sections also include resilient metallic clasps 24 which are embedded in the upper and lower sections, and which engage the teeth. The clasps engage the teeth, and serve to hold the upper and lower sections firmly engaged with the teeth. The clasps may be similar to those disclosed in U.S. Pat. No. 3,837,081.

The action of elastics 16 may be augmented by permanent magnet forces, or replaced by permanent magnet forces, if so desired. Also, the action of the clasps 24 may be augmented by small suction cups (not shown) mounted within the archways 11 and 12.

The particular feature of the positioner assembly shown in the drawing is that because it has two separate sections related in traction by elastic or magnetic forces, which cause the sections to come together and to be properly aligned by the guides 20 and corresponding guideways 22, and the sections being retained on the teeth of the maxillary and mandibular arches by the metallic clasps 24 set into the material of the positioner, as shown, assisted, for example, by tiny suction cups embedded in the positioner material.

Figure 1:
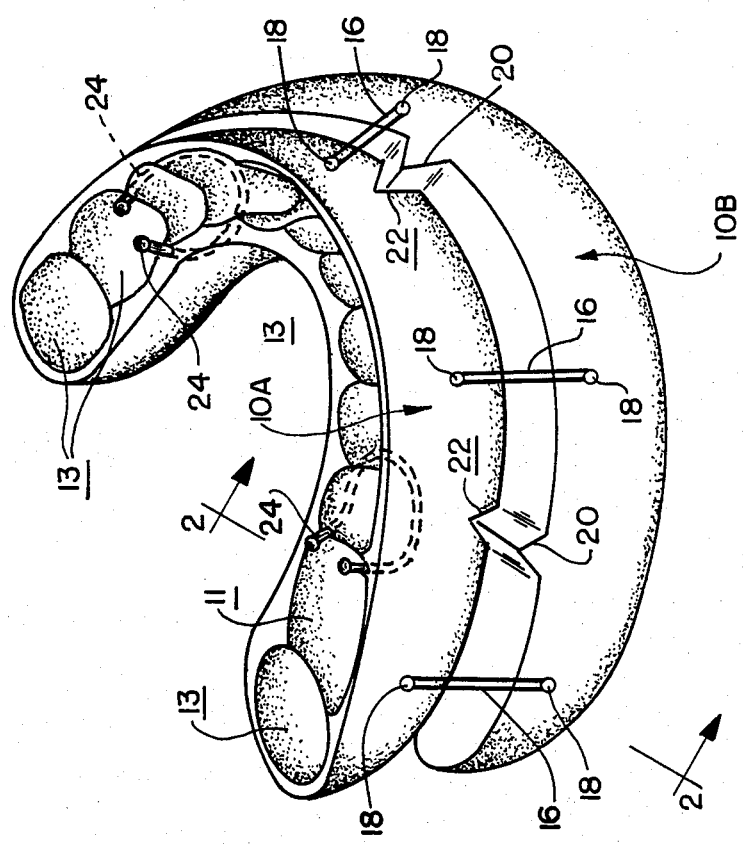
FIG. 1 is a perspective representation of a split orthodontic positioner constructed in accordance with one embodiment of the invention.

Accordingly, the positioner assembly shown in FIGS. 1 and 2 is constructed in a manner that the two separate sections are attached to the teeth, and are forced together by elastic or magnetic traction, so as to cause better and faster arch coordination and occlusion seating.

If so desired, the positioner assembly can be fitted with vibrational apparatus of the type described and claimed in U.S. Pat. No. 4,123,844 which issued Nov. 7, 1978 to the present inventor.

It will be appreciated that while a particular embodiment of the invention has been shown and described, modifications may be made. It is intended in the claims to cover all modifications which come within the spirit and scope of the invention.

What is claimed is:

1. A pre-formed orthodontic tooth positioning and retaining appliance comprising: a molded two-piece arch-shaped body of resilient material having an upper section and a lower section, said upper section having an archway formed on its top surface with a plurality of tooth sockets therein for receiving the teeth of the maxillary arch of a patient, said lower section having an archway formed in its bottom surface with a plurality of tooth sockets therein for receiving the teeth of the mandibular arch of the patient; and resilient means connected to the upper and lower sections for biasing the sections together in a traction relationship.

2. The pre-formed tooth positioning and retaining appliance defined in claim 1, in which said resilient means comprises a plurality of elongated resilient members, and hooks for connecting the respective ends of each of the resilient members to corresponding ones of said upper and lower sections.

3. The pre-formed tooth positioning and retaining appliance defined in claim 1, and which includes a plurality of clasp-like members embedded in at least one of said sections for engaging the teeth of the corresponding arch, firmly to retain the teeth in the section.

4. The pre-formed tooth positioning and retaining appliance defined in claim 3, and which includes a plurality of said clasps mounted in each of said sections for engaging the teeth of both the maxillary and mandibular arches of the patient.

5. The pre-formed tooth positioning and retaining appliance defined in claim 1, and which includes guide means formed on the two sections so that the sections may be guided into a predetermined relationship with one another as the sections are biased together by the resilient members.

* * * * *